United States Patent [19]  
White et al.

[11] 4,021,550  
[45] May 3, 1977

[54] HEXAHYDROAZEPINES AS ANTIINFLAMMATORY AGENTS
[75] Inventors: Alan Chapman White, Windsor; Richard Arthur Franklin, Twyford, both of England
[73] Assignee: John Wyeth & Brother Limited, Maidenhead, England
[22] Filed: June 7, 1976
[21] Appl. No.: 693,665
[30] Foreign Application Priority Data
June 18, 1975 United Kingdom ............ 25891/75
[52] U.S. Cl. .......................... 424/244; 260/239 B; 260/239 BF
[51] Int. Cl.² ....................................... C07D 223/04
[58] Field of Search ............... 260/239 BF; 424/244
[56] References Cited
UNITED STATES PATENTS
3,729,465  4/1973  Cavalla et al. ................. 260/239 B Primary Examiner—Raymond V. Rush

[57] ABSTRACT

The invention concerns hexahydroazepines of the formula

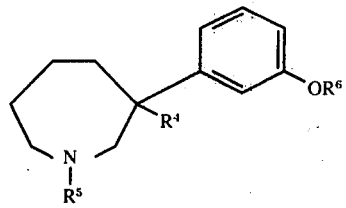

and the pharmaceutically acceptable acid addition and quaternary ammonium salts thereof, wherein $R^4$ is lower alkyl, $R^5$ is lower alkyl, lower alkenyl, lower alkynyl or cyclopropylmethyl and $R^6$ is a 1-adamantoyl group. The compounds are useful as analgesic agents.

5 Claims, No Drawings

HEXAHYDROAZEPINES AS ANTIINFLAMMATORY AGENTS

This invention relates to novel hexahydroazepines, to processes for their preparation and to pharmaceutical compositions containing them.

U.K. Specification No. 1,285,025 describes hexahydroazepines of the general formula (I)

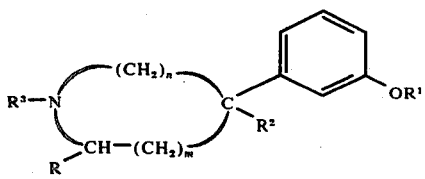

and the acid addition and quaternary ammonium salts thereof, in which $R^1$ is a hydrogen atom, a lower alkyl radical, a benzyl radical or a lower alkanoyl radical, $R^2$ is a lower alkyl radical, $R^3$ is a hydrogen atom, a lower alkyl, lower alkenyl, lower alkynyl, cyclopropylmethyl, lower alkanoyl, lower alkoxycarbonyl, formyl, phenacyl or phenethyl group both of which may be substituted in the benzene ring or a β-benzoylethyl radical which may be substituted in the benzene ring, n is 3 or 4, m is 0 or 1 with the proviso that $n + m$ is always equal to 4, R is a hydrogen atom or a lower alkyl radical when m is 0, or a hydrogen atom only when m is 1, and the term "lower" means that the radical contains up to 6, preferably up to 4 carbon atoms.

The present invention relates to adamantoate esters of certain of the above compounds of general formula I in which $R^1$ is a hydrogen atom. Accordingly the present invention provides a hexahydroazepine of the general formula (II)

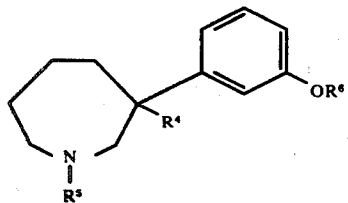

and the pharmaceutically acceptable acid addition and quaternary ammonium salts thereof, wherein $R^4$ is lower alkyl, $R^5$ is lower alkyl, lower alkenyl, lower alkynyl or cyclopropylmethyl and $R^6$ is a 1-adamantoyl group.

In the compounds of the invention $R^4$ can be, for example, a lower alkyl group such as methyl, ethyl, propyl or butyl. Preferably $R^4$ is ethyl.

$R^5$ can be lower alkyl (e.g. methyl, ethyl, propyl or butyl), lower alkenyl (e.g. allyl, 2-methylallyl or 3-methyl-2-butenyl), lower alkynyl (e.g. 2-propynyl) or cyclopropylmethyl. $R^5$ is preferably lower alkyl, e.g. methyl.

$R^6$ is a 1-adamtantoyl group i.e. a group of the formula

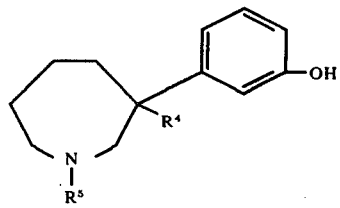

The compounds of the invention can be prepared by esterifying a compound of general formula (III)

(wherein $R^4$ and $R^5$ have the meanings given above) with a reactive derivative of adamantane-1-carboxylic acid. Alternative names for adamantane-1-carboxylic acid include adamantoic acid and tricyclo [3.3.1.1.$^{3,7}$]decane-1-carboxylic acid. In a preferred process of the invention the compound of formula (III) is esterified with the acid chloride of adamantane-1-carboxylic acid, for example in an organic solvent in presence of a base (e.g. triethylamine). Alternative reactive derivatives of adamantane-1-carboxylic acid include the anhydride and suitable mixed anhydrides e.g. with trifluoracetic acid or with an alkyl acid carbonate.

If in the process described above the compound of the invention is obtained as an acid addition salt, the free base can be obtained by basifying a solution of the acid addition salt. Conversely, if the product of the process is a free base, an acid addition salt, particularly a pharmaceutically acceptable acid addition salt may be obtained by dissolving the free base in a suitable organic solvent and treating the solution with an acid, in accordance with conventional procedures for preparing acid addition salts from base compounds.

Examples of acid addition salts are those formed from inorganic and organic acids such as sulphuric, hydrochloric, hydrobromic, phosphoric, tartaric, fumaric, maleic, citric, acetic, formic, methanesulphonic and p-toluenesulphonic acids. A quaternary ammonium salt may be prepared by reacting the free base with for example an alkyl halide.

The starting materials of general formula (III) are described in U.K. Specification Nos. 2,285,025 and 1,319,785 Adamantane-1-carboxylic and its functional derivatives are also described in the literature or may be prepared by methods known for the preparation of analogous compounds.

The compounds of the invention possess an asymmetric carbon atom in the molecule and hence they can exist in various stereochemical forms. In particular, the invention provides the optically active isomers and mixtures of such isomers, particularly the racemate. It will be realised that if the starting material of formula (III) is in the form of an optically active isomer the product of the process of the invention will also be an optically active isomer while if the starting material is, for example, a racemate the product of the process will also be a racemate.

The compounds of the invention possess analgesic activity as indicated upon administration to warm blooded animals according to a standard pharmacological procedure. One such procedure for measuring analgesic activity is a modification of the Rat Tail Flick procedure of D'Amour and Smith, J. Pharmacol., 1941, 72, 74. The test material is administered to rats at varying dosage levels and the dose which produces 50% of total possible analgesic responses in the experimental period is determined. It was found that tricyclo[3.3.1.1.$^{3,7}$]decene-1-carboxylic acid-3-(3-ethyl hexahydro-1-methyl-1H-azepin-3-yl) phenyl ester, i.e. a representative compound of formula II in which $R^4$ is ethyl and $R^5$ is methyl, produces 50% of total possible analgesic responses at 17 mg/kg when administered subcutaneously and at 35 mg/kg when administered orally. This compound has the advantage of a better oral/subcutaneous dose ratio than the corresponding unesterified compound, m-(3-ethylhydro-1-methyl-1H-azepin-3-yl)phenol.

The invention further provides a pharmaceutical composition which comprises a compound of general formula (II) or a pharmaceutically acceptable acid addition or quaternary ammonium salt thereof, in association with a pharmaceutically acceptable carrier. In such a composition, the carrier may be a solid, liquid or mixture of a solid and a liquid. Solid form compositions include powders, tablets and capsules. A solid carrier can be one of more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredients. In tablets the active ingredient is mixed with a carrier having the necessary binding properties in suitable proportions and compacted in the shape and size desired. The powders and tablets preferably contain from 5 to 99, preferably 10-80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can be dissolved in a suitable organic solvent, for instance aqueous propylene glycol containing from 10 to 75% of the glycol by weight is generally suitable.

In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspension can be utilized by intramuscular, intraperitoneal or subcutaneous injection. In many instances a compound is orally active and can be administered orally either in liquid or solid composition form.

Preferably the pharmaceuticaly composition is in unit dosage form. In such form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule or tablet itself, or it can be the appropriate number of any of these in packaged form. The quantity of active ingredient in a unit dose of composition may be varied or adjusted from about 5 mg. to 500 mg, according to the particular need and the activity of the active ingredient. The invention also includes the compounds in the absence of carrier where the compounds are in unit dosage form. The daily dose of compound will vary depending upon the route of administration, the particular compound employed and the particular animal involved.

The following Example illustrates the invention.

EXAMPLE 1

Tricyclo [3.3.1.1.$^{3,7}$]decane-1-carboxylic acid-3-(3-ethyl hexahydro-1-methyl-1H-azepin-3-yl)phenyl ester Tricyclo [3.3.1.1.$^{3,7}$]decane-1-carboxylic acid chloride (1.98 g) in methylene dichloride (5 ml) was added dropwise to a stirred solution of 3-(3-ethyl-1-methyl-1H-hexahydroazepin-3-yl)phenol (2.3 g) in methylene dichloride (20 ml) containing triethylamine (1.42 ml) at 0° C. The reaction mixture was stirred at room temperature for 16 hours then washed with water and 2N sodium bicarbonate solution. After drying the solvent was removed and the product was treated with isopropanol and hydrogen chloride in dry ether. The title compound was obtained as colourless needles as its hydrochloride salt 2.52g m.p. 138°–142° C. (Found: C 70.4; H, 9.05; N 3.3. $C_{26}H_{37}NO_2 \cdot HCl \cdot \frac{1}{2}H_2O$ requires C 70.8; H, 8.9; N 3.2%).

EXAMPLE 2

1-Tricyclo[3.3.1.1.$^{3,7}$]decane-1-carboxylic acid-3-(1-cyclopropylmethyl-3-ethyl-1H-azepin-3-yl)phenyl ester.

1-3-(1-Cyclopropylmethyl-3-ethylhexahydro-1H-azepin-3-yl) phenol fumarate (1.98g) was converted to the free base by suspending in water (10 ml) and treating with 2N sodium carbonate solution until strongly alkaline. The resulting solution was extracted with methylene dichloride (3 × 10 ml) and dried (MgSO4). After filtration the solution was evaporated to give 5mM of the base.

The base was dissolved in methylene chloride (10 ml) and triethylamine (0.62 ml) and the solution then treated with a solution of adamantane carboxylic acid chloride (1.0 g). After stirring overnight at room temperature the reaction mixture was washed with water (3 × 10 ml) dried (MgSO4) and the solvent removed to leave an oil which afforded the title material hydrobromide (1.56 g), m.p. 236°–8° C (decomp) from isopropanol/hydrogen bromide in dry ether. Recrystallisation from absolute ethanol/ether raised the m.p. to 240°–241° C(decomp). (Analysis: Found C 67.4; H 8.35; N, 2.7. $C_{29}H_{41}NO_2 \cdot HBr$ requires C 67.4; H, 8.2; N 2.7%).$[\alpha]_D^{24}$ —26.7° (c 1% in water).

EXAMPLE 3

Following the procedure of Example 1 the following phenols are reacted with tricyclo[3.3.1.1.$^{3,7}$]decane-1-carboxylic acid chloride to give the corresponding products:

| | Phenol | Product |
|---|---|---|
| (a) | m-(1-allyl-3-ethyl-1H-azepin-3-yl phenol | Tricyclo[3.3.1.1.$^{3,7}$]decane-1-carboxylic acid-3-(1-allyl-3-ethylhexahydro-1H-azepin-3-yl phenyl ester |
| (b) | m-[3-ethylhexahydro-1-(2-propynyl)-1H-azepin-3-yl]phenol | Tricyclo[3.3.1.1.$^{3,7}$]decane-1-carboxylic acid-3-[3-ethyl-hexahydro-1-(2-propynyl)-1H-azepin-3-yl]phenyl ester |
| (c) | m-(1,3-diethylhexahydro-1H-azepin-3-yl)phenol | Tricyclo[3.3.1.1.$^{3,7}$]decane-1-carboxylic acid-3-(1,3-diethylhexahydro-1H-azepin-3-yl)phenyl ester |

We claim:

1. A compound selected from the group consisting of a hexahydroazepine of formula

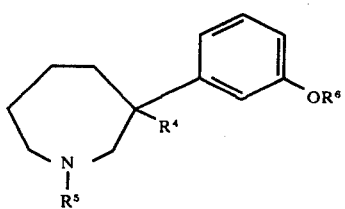

(II)

and a pharmaceutically acceptable acid addition or quaternary ammonium salt thereof, wherein $R^4$ is lower alkyl, $R^5$ is lower alkyl, lower alkenyl, lower alkynyl or cyclopropylmethyl and $R^6$ is a 1-adamantoyl group.

2. A compound according to claim 1 wherein $R^4$ is ethyl and $R^5$ is lower alkyl.

3. A compound according to claim 1 which is tricyclo[3.3.1.1.$^{3,7}$]decane-1-carboxylic acid-3-(3-ethyl hexahydro-1-methyl-1H-azepin-3-yl)phenyl ester.

4. A compound according to claim 1 which is 1-tricyclo[3.3.1.1.$^{3,7}$]decane-1-carboxylic acid-3-(1-cyclopropylmethyl-3-ethyl-1H-azepin-3-yl)phenyl ester.

5. A pharmaceutical composition having analgesic activity comprising an analgesically effective amount of a compound selected from the group consisting of a hexahydroazepine of formula

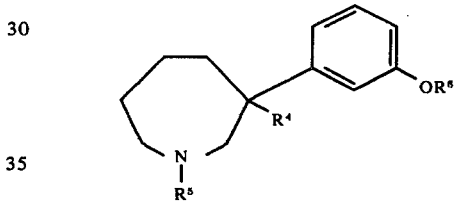

(II)

and a pharmaceutically acceptable acid addition or quaternary ammonium salt thereof, wherein $R^4$ is lower alkyl, $R^5$ is lower alkyl, lower alkenyl, lower alkynyl or cyclopropylmethyl and $R^6$ is a 1-adamantoyl group in association with a pharmaceutically acceptable carrier.

* * * * *